United States Patent [19]

Bolle et al.

[11] 4,284,520

[45] Aug. 18, 1981

[54] STABLE AND NON-CORROSIVE POLYSULPHIDES DERIVED FROM OLEFINS AND HAVING DIFFERENT SULPHUR CONTENTS, PROCESS FOR THEIR MANUFACTURE AND APPLICATIONS THEREOF

[75] Inventors: Jean Bolle, Evaux les Bains; Andre Dabir, Paris, both of France

[73] Assignee: Institut National de Recherche Chimique Appliquee, France

[21] Appl. No.: 39,245

[22] Filed: May 15, 1979

[51] Int. Cl.³ .................... C10M 1/39; C10M 3/32
[52] U.S. Cl. ..................................... 252/45; 260/139
[58] Field of Search ........................... 252/45; 260/139

[56] References Cited

U.S. PATENT DOCUMENTS

| | | | |
|---|---|---|---|
| 2,249,312 | 7/1941 | Kimball | 252/48.8 |
| 3,703,504 | 11/1972 | Horodysky | 260/139 |
| 3,703,505 | 11/1972 | Horodysky et al. | 260/139 |
| 4,147,640 | 4/1979 | Jayne et al. | 252/45 |

OTHER PUBLICATIONS

Journal of the Chemical Society, Article by Bateman et al., p. 2838, 1958.

*Primary Examiner*—Delbert E. Gantz
*Assistant Examiner*—Irving Vaughn
*Attorney, Agent, or Firm*—Karl W. Flocks

[57] ABSTRACT

These polysulphides are derived from at least two olefins and are suitable as lubricating and industrial oil additives. They have a proportion of sulphur of 22 to 45% for a practically zero content of chlorine and a refractive index $n_D^{20}$ ranging from 1.515 to 1.580.

3 Claims, 1 Drawing Figure

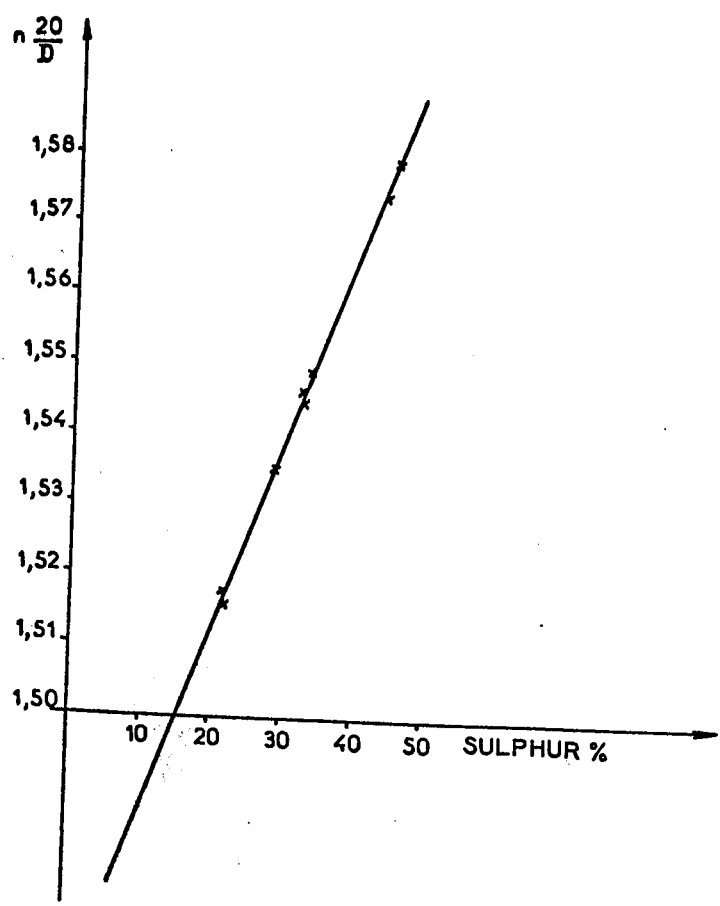

STABLE AND NON-CORROSIVE POLYSULPHIDES DERIVED FROM OLEFINS AND HAVING DIFFERENT SULPHUR CONTENTS, PROCESS FOR THEIR MANUFACTURE AND APPLICATIONS THEREOF

BACKGROUND OF THE INVENTION

1. Field of the Invention

The present invention relates to stable and non-corrosive polysulphides derived from at least two olefins, suitable as additives for lubricating and industrial oils and to their process of manufacture.

According to a particular embodiment of this process, the invention relates also to the products obtained from isobutylene and diisobutylene used as starting olefins.

2. Description of the Prior Art

The presently known olefin polysulphides suitable as additives for oils have a particular sulphur content according to the nature of the starting materials. This sulphur content is not variable at will and numerous known processes do not permit a whole range of polysulphides to be available having, for example, a proportion of sulphur of 22 to 45%.

All these processes apply the two following principal reactions, namely: (1) reaction of a sulphur chloride with the starting olefin compound and (2) treatment of the resulting product with an alkali metal sulphide.

The reaction conditions vary from one process to the next. The starting olefin compound may be constituted by a single olefin, by a mixture of olefins, or of olefins and hydrocarbons. Such processes are, for example, described in U.S. Pat. Nos. 2,249,312; 3,471,404; 3,068,218; 3,697,499; 3,703,505; 3,703,504. The products resulting from the process described in U.S. Pat. No. 2,249,312 have generally a non-negligible proportion of chlorine, the proportion of sulphur depending to a high degree on the nature of the one or more starting olefins. U.S. Pat. No. 3,471,404 describes a process consisting of reacting sulphur monochloride with the olefin compound and treating the product resulting from this reaction with an alkali metal sulphide and free sulphur, then reacting the resulting product with an aqueous solution of a mineral base to lower the final proportion of chlorine. Although the exact structure of the final product is not known, it is specified in the patent that this product may consist of monomers containing sulphur or of monomers coupled together by a sulphur bridge to form a cyclic structure; it is thought that about 75% of the product, or more, consists of monomeric sulphur and of their cyclic derivatives.

The process described in U.S. Pat. No. 3,068,218 consists of reacting sulphur chloride with an olefin hydrocarbon in the presence of a mixture of water and an oxygen-containing organic compound miscible with water of the type of alcohol, acetone, or aldehyde. The chlorine content of the final product is far from being negligible and may be prejudicial to the result expected in the application of this product as an additive to lubricating oils.

As for U.S. Pat. No. 3,697,499, this patent describes a process in which sulphur monochloride is reacted with an olefin compound, treating the resulting product by means of an alkali metal sulphide in the presence of free sulphur in a solvent medium comprising an alcohol and water, then reacting the product resulting therefrom with a mineral base. The final product, although the exact structure is unidentified, includes, it is thought, cyclic units.

U.S. Pat. No. 3,703,505 describes a process consisting of subjecting an olefin hydrocarbon to sulphohalogenation by means of sulphur chloride to form a sulphochlorinated organic intermediate, then proceding with sulphuration and dehalogenation on the intermediate product by reaction with an alkali metal sulphide, the process being applied with the addition of a base enabling the formation of a colored product to be avoided, this base being of the amide, hydroxide, carbonate, bicarbonate or acetate of alkali metal type. The chlorine content of the one or more products obtained according to this process remains all the same of the order of 0.2 to 0.5%.

Finally, U.S. Pat. No. 3,703,504 describes a process consisting of reacting the olefin hydrocarbon with sulphur monochloride in the presence of an alcohol to form a sulphochlorinated intermediate product which is then reacted, in the presence of a relatively large amount of isopropanol, with an aqueous solution of sodium monosulphide derived from spent petroleum refinery liquors. The sulphur content of the products resulting from this process is high for a relatively low chlorine content (of the order of 0.1%).

All these processes may be applied to a single type of olefin or to mixtures of olefins. They do not however permit the sulphur content to be varied at will.

It is an object of the present invention to enable the proportion of sulphur to be varied and, in the particular case of its application to isobutylene and to diisobutylene taken as starting olefins, to provide a whole range of polysulphide products having a proportion of sulphur of 22 to 45% for a proportion of chlorine in the vicinity of zero, i.e. substantially zero.

GENERAL DESCRIPTION OF THE INVENTION

Although the reaction which is relied upon for producing the products according to the invention, namely, that bringing into play sulphur chloride which is reacted with the one or more olefins, and then sodium monosulphide, the process according to the invention is characterized essentially by the conditions in which these reactions are carried out, namely, that in a first step one of the two olefins is treated with sulphur monochloride, that in a second step, there is run into the preceding mixture the desired amount of the second olefin and a new amount of sulphur monochloride is added, and that finally, sodium sulphide is reacted with the reaction medium resulting from the second step. By proceeding in this manner, there are obtained, at will, polysulphides having proportions of sulphur varying with the proportions of the two olefins employed.

In the particular case of isobutylene and of diiosobutylene, taken as starting olefins, the isobutylene is advantageously introduced in the first step, to add the diisobutylene in the second step, it being well understood that it is possible to contemplate the admission firstly of the diisobutylene in the first step and the isobutylene in the second.

The products derived directly from the process according to the invention are, in addition, characterized by the fact that they have a practically zero content of chlorine, a sulphur content of 22 to 45% for a refractive index $n_D^{20}$ varying from 1.515 to 1.580, which index is a linear function of the proportion of sulphur as illustrated in the accompanying diagram (FIG. 1), established by plotting as abcissae the sulphur proportion and, as ordinates, the refractive index. The products of the invention are characterised by an average molecular weight variable according to the composition but which is situated preferably between 300 to 600. The ash content is practically zero and a Luchaire inflammability temperature higher than 90° C.

DESCRIPTION OF A PREFERRED EMBODIMENT

The following example is given purely by way of non-limiting illustration of the invention.

EXAMPLE

In a first step, a flow of isobutylene ($C_4H_8$) is passed into 100 kg of $S_2Cl_2$ until refusal; the reaction being slightly exothermic, it is not necessary to cool very much in order to remain at room temperature. A flow of nitrogen or of argon is then passed into the mixture to remove completely the traces of hydrogen chloride formed. There is thus obtained about 170 kg of a crude product (A), having a sulphur content close to 30% and scarcely less of chlorine.

To 170 kg of this crude product (A) resulting from the first step above, is added about 260 kg of diisobutylene ($C_8H_{16}$), the mixture is heated to 55°-60° C., and about 100 kg of sulphur monochloride is run in slowly, with stirring. Stirring is continued under a flow of inert gas to remove the hydrogen chloride formed. There is thus obtained about 525 kg of a product (B), resulting from the second sulphochlorination step.

In a third step, the 525 kg of (B) are dechlorinated by the action of sodium sulphide: a filtered solution of about 190 kg of sodium sulphide in flakes, with at least 60% of $Na_2S$, is added slowly (about 4 hours) at ambient temperature, in about 1,300 liters of pure methyl alcohol. The mixture is then boiled under reflux (60°-70° C.) for at least 2 hours. After removal of the sodium chloride formed, the methanol is removed by flash distillation.

The residual liquid (C) is taken up by means of about 760 liters of petroleum ether boiling between 30° and 75° C. (G gasoline). After stirring at ordinary temperature, there remained an insoluble part which is removed by filtration or decantation. The resulting solution is washed several times with water, then dried, and the solvent is removed by flash distillation for recycling.

There remained a yellow-amber, oily product, having a slight sweetish sulphur smell, which constitutes the desired product: (D).

The product is a complex mixture which results, on the one hand, from the addition of sulphur monochloride to the double bonds of the olefins, on the other hand, from substitution, and then from formation of sulphur bridges at the moment of removal of the chlorine by the sodium sulphide. The ultraviolet absorption spectra show that rings or sulphur heterocyclic rings are not present. The infrared spectra and nuclear magnetic resonance spectra show the abundance of tertiary butyl groups and the residual unsaturation of the products obtained.

According to the proportion of the isobutylene and of diisobutylene employed, the mixture may be modified and, in particular, the proportion of sulphur ($t_s$) can vary from 22 to 45% by weight. The latter may be estimated easily by measurement of the refractive index ($n_D^{20}$) of the final product (D), which is related to the proportion of sulphur ($t_s$) by the relationship:

$$n_D^{20} = 2.63 \times 10^{-3} t_s + 1.4606$$

In the example described above of the manufacture of the product (D), a typical but in no way limiting example, the percentage composition is close to:

% C: 55.6
% H: 9.14
% S: 32.4
% Cl: 0.03
% N: 0

The average molecular weight of the mixture, which varies also with the composition, is of the order of 350. The proportion of ash is very low (0.015%). The absolute dynamic viscosity (measured according to NF 60/100) is:

144 centipoises at 25° C.
38 centipoises at 50° C.

whilst the kinematic viscosity is:

1.38 stokes at 25° C.
0.37 stokes at 50° C.

and the refractive index $n_D^{20} = 1.5461$ and the Luchaire inflammability point (according to NF 60/103) is higher than 90° C. in closed and open cup.

The products according to the invention are stable and non-corrosive. Moreover they are characterised by a faint smell and a slight colour. Also they present good performance in mechanical tests such as extreme pressure (E.P) test, oxidation test, seizing threshold, weld load, load wear index and anti-wear tests. Some data resulting from said tests carried out on the product obtained such as described above appear from the following tables.

Therefore the products according to the invention are particularly interesting as additives for extreme pressure lubricating oils, outside motor oils. In this field, they are used in the same proportions as known additives of the family of sulphurated olefins, even in smaller proportions whilst leading to better characteristics of the final oil.

In addition, contrary to known additives of this same family, the compounds of the invention find advantageous applications in industrial oils for improving the properties thereof.

TABLE I

This table summarises the principal properties such as Extreme Pressure (E.P), oxidative resistance of the product according to the invention. It shows usual known phenomenon for certain types of polysulphide ie. when the concentration of the polysulphide is increased, the E.P performance decreases, particularly the seizing threshold decreases in the four balls machine test and the wear increases in the Falex machine test.

E.P Properties

Four Balls Machine Test (ASTM D 2783)
Base oil: SAE 90 CFR.

| % Polysulphide | Seizing load (kg) | Weld load (kg) |
|---|---|---|
| 6.5 | 70 | >300 |
| 3 | 80 | >300 |

FALEX Test (ASTM D 3233)

| % Polysulphide | Breaking load (lbs) | Wear after 30 min. under 500 lbs. load (mg) |
| --- | --- | --- |
| 6.5 | 950 | 14 |
| 9 | 950 | 60 |

Oxidative resistance—MOBIL Test (MAO 91)

| % Polysulphide | Viscosity variation at 100° F. | I.R Absorption at 1715 cm$^{-1}$ |
| --- | --- | --- |
| 6.5 | 47.2 | 0.74 |

Corrosion Test ASTM D 130
Pure Product: 4b
3% in oil (SAE 90 CFR): 1b
Determination of active sulphur (ASTM D 1662)

| Temperature °C. | % of active S |
| --- | --- |
| 100 | 4 |
| 150 | 30 |
| 180 | 75 |

TABLE II

This table compares the product of the invention per se (P.I) with formulations comprising said product with phosphorated and anti-oxidizing agents usually applied for gearing oil formulations complying with the MIL-L 2105 B specifications.

Formulation Used

Base oil (SAE 90)+PI alone
or Base oil+PI+6.5% phosphorated compound 1+antioxidizing agent (PI+DP1)
or Base oil+PI+6.5 phosphorated compound 2+antioxidizing agent (PI+DP2)

|  | % | FALEX test Breaking load lbs | Wear (mg) | Four ball test Seizing load (kg) |
| --- | --- | --- | --- | --- |
| P.I | 6.5 | 950 | 14 | 80 |
| P.I | 9 | 950 | 60 |  |
| P.I + DP1 | 6.5 | 2350 | 5 | 110 |
| P.I + DP2 | 6.5 | 3400 | 1 |  |

|  | % | Oxidation test Viscosity Variation dv (%) v | I.R absorption (absorbance) |
| --- | --- | --- | --- |
| P.I | 6.5 | 47.2 | 0.74 |
| P.I | 9 | 59 | 0.82 |
| P.I + DP1 | 6.5 | 41.1 | 0.72 |
| P.I + DP2 | 6.5 | 31.2 | 0.57 |

TABLE III

This table compares three different polysulphides.
The product of the invention: P.I: 32.4% S
Adduct 1: 17% S containing an ester
Adduct 2: 47.5% S.

| Falex Test | Wear (mg) | Breaking (lbs) |
| --- | --- | --- |
| P.I + Ester | 3.9 | 2,700 |
| Adduct 1 | 2.8 | 1,200 |
| Adduct 2 + Ester | 7.3 | 2,300 |

TABLE IV

This table gives the content of active sulphur with respect to the temperature.
The active sulphur content appears in Table I.
The S content of the oil used was 1.5%.

| % S removed | Falex test Wear (mg) | Falex test Breaking (lbs) | Four balls test Wear ($1^h$-40kg) (min) | Four balls test Weld (kg) |
| --- | --- | --- | --- | --- |
| 0 | 60 | 1,025 | 0.85 | 390 |
| 4 | 24 | 1,050 | 0.8 | 390 |
| 30 | 20 | 1,180 | 0.8 | 385 |
| 72 | 13 | 1,550 | 0.75 | 250 |

It is self-evident that the present invention has only been described in purely explanatory and non-limiting manner, and that any modification in the way of equivalents could be applied thereto without departing from its scope as defined by the appended claims. Thus, in particular, it is possible to obtain a range of products by modifying the proportions of isobutylene and of diisobutylene in the preceding examples.

We claim:

1. Stable and non-corrosive polysulphide derived from isobutylene and diisobutylene, suitable as lubricating and industrial oil additive, having a sulphur content from 22 to 45% for a substantially zero content of chlorine and a corresponding refractive index $n_D^{20}$ from 1.515 to 1.580, the molecular structure of said polysulphide including residual unsaturations having no rings or sulphur-containing heterocyclic rings, said polysulphide having a molecular weight of 300 to 600, a practically zero ash content and a Luchaire inflammability temperature higher than 90° C.

2. A process for selectively manufacturing polysulphides according to claim 1 having a quantity of sulphur from 22 to 45% and substantially zero content of chlorine, and a corresponding refractive index of 1.515 to 1.580, comprising
   in a first step, forming a first intermediate by adding, until refusal, isobutylene to sulphur monochloride at ambient temperature;
   in a second step, running diisobutylene into said first intermediate, adding additional sulphur monochloride, and reacting said first intermediate, said diisobutylene and said additional sulphur monochloride under the application of heat to form a second intermediate; and
   reacting said second intermediate with sodium sulphide and separating the resultant polysulphide.

3. Stable and non-corrosive polysulphide produced directly by the process according to claim 2.

* * * * *